US009905217B2

(12) United States Patent
Hyde et al.

(10) Patent No.: US 9,905,217 B2
(45) Date of Patent: Feb. 27, 2018

(54) ACTIVE CANCELLATION OF NOISE IN TEMPORAL BONE

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, Seattle, WA (US); Richard T. Lord, Gig Harbor, WA (US); Robert W. Lord, Seattle, WA (US); Clarence T. Tegreene, Mercer Island, WA (US); Yaroslav A. Urzhumov, Bellevue, WA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 245 days.

(21) Appl. No.: 14/523,000

(22) Filed: Oct. 24, 2014

(65) Prior Publication Data

US 2016/0118035 A1 Apr. 28, 2016

(51) Int. Cl.

| | |
|---|---|
| ***A61F 11/06*** | (2006.01) |
| ***G10K 11/178*** | (2006.01) |
| ***H04R 1/10*** | (2006.01) |
| *H04R 3/00* | (2006.01) |

(52) U.S. Cl.

CPC ......... *G10K 11/178* (2013.01); *H04R 1/1083* (2013.01); *G10K 2210/129* (2013.01); *H04R 3/005* (2013.01); *H04R 2201/107* (2013.01); *H04R 2410/05* (2013.01); *H04R 2460/01* (2013.01); *H04R 2460/13* (2013.01)

(58) Field of Classification Search

CPC . G10K 11/175; H04R 1/1091; H04R 2460/01
USPC ................................................ 381/151, 71.6
See application file for complete search history.

(56) References Cited

U.S. PATENT DOCUMENTS

| | | | | |
|---|---|---|---|---|
| 5,570,426 | A | 10/1996 | Gardner | |
| 6,466,673 | B1 | 10/2002 | Hardy | |
| 8,325,964 | B2 | 12/2012 | Weisman | |
| 2006/0029246 | A1 * | 2/2006 | Boesen | H04M 1/6066 381/326 |
| 2009/0304210 | A1 | 12/2009 | Weisman | |
| 2011/0293105 | A1 | 12/2011 | Arie et al. | |
| 2013/0142348 | A1 | 6/2013 | Weisman | |
| 2014/0029762 | A1 * | 1/2014 | Xie | H04R 5/027 381/94.1 |
| 2014/0072148 | A1 * | 3/2014 | Smith | H04R 1/08 381/151 |
| 2015/0170633 | A1 * | 6/2015 | Nakagawa | G10K 11/175 381/71.6 |
| 2016/0100260 | A1 * | 4/2016 | Ruppersberg | H04R 25/453 381/326 |

* cited by examiner

*Primary Examiner* — Vivian Chin
*Assistant Examiner* — Ammar Hamid
(74) *Attorney, Agent, or Firm* — Foley & Lardner LLP

(57) ABSTRACT

A noise-canceling device includes a processing circuit configured to detect vibrational noise sound waves near a listener's ear using a vibration sensor, generate a vibrational noise-canceling signal, and control operation of a speaker to provide a desired sound signal and the vibrational noise-canceling signal to at least partially cancel the vibrational noise sound waves.

38 Claims, 8 Drawing Sheets

ACTIVE CANCELLATION OF NOISE IN TEMPORAL BONE

BACKGROUND

Noise-canceling earphones are used to provide desired sound signals to a listener while reducing unwanted external noises. Passive noise reduction techniques physically prevent sound waves from reaching a listener's ear by using insulation or dampening (e.g., an earcup that surrounds or rests on the ear) to reduce undesired sounds from interfering with a desired sound signal. However, these techniques are best at reducing middle and high frequencies. To further reduce unwanted external noises, some earphones use active noise cancellation techniques, a process for reducing unwanted sound through destructive interference, by adding an additional out-of-phase sound designed to cancel the unwanted sound.

SUMMARY

One embodiment relates to a noise-canceling earphone that includes a processing circuit. The processing circuit is configured to detect vibrational noise sound waves near a listener's ear using a vibration sensor, generate a vibrational noise-canceling signal, and control operation of a speaker to provide a desired sound signal and the vibrational noise-canceling signal to at least partially cancel the vibrational noise sound waves.

Another embodiment relates to a noise-canceling earphone that includes a processing circuit. The processing circuit is configured to detect vibrational noise sound waves near a listener's ear using a vibration sensor, detect ambient noise using a microphone, generate a vibrational noise-canceling signal, generate an ambient noise-canceling signal, and provide the vibrational noise-canceling signal, the ambient noise-canceling signal, and a desired sound signal to a speaker.

Another embodiment relates to a noise-canceling earphone that includes a processing circuit. The processing circuit is configured to receive a plurality of inputs, including a first input based on a vibration traveling toward a listener's ear, a second input based on a vibration traveling away from the listener's ear, a third input based on a sound traveling toward the listener's ear, and a fourth input based on a sound traveling away from the listener's ear; determine a noise mitigation signal to at least partially cancel the first input and the third input; and control operation of a speaker to provide the noise mitigation signal and a desired sound signal.

Another embodiment relates to a noise-canceling earphone that includes a speaker and a processing circuit. The speaker is configured to play a desired sound signal and a noise mitigation signal, wherein the noise mitigation signal is generated by a processing circuit coupled to at least one vibration sensor and coupled to at least one microphone. The processing circuit is configured to detect the phase, amplitude, and direction of vibrational noise sound waves near a listener's ear using at least one vibration sensor; detect the phase, amplitude, and direction of ambient noise using at least one microphone; generate the noise mitigation signal based on the phase, amplitude, and direction of the vibrational noise sound waves and the ambient noise; and to feed the noise mitigation signal and the desired sound signal to the speaker.

Another embodiment relates to a method for canceling vibrational noise sound waves detected in a listener's temporal bones. The method includes receiving a signal regarding undesired vibrational noise sound waves at a processing circuit; generating, by the processing circuit, a vibrational noise-canceling signal; and controlling, by the processing circuit, a speaker to provide a desired sound signal and the vibrational noise-canceling signal.

Another embodiment relates to a method for canceling vibrational noise sound waves detected in a listener's temporal bones. The method includes detecting vibrational noise sound waves near a listener's ear using a vibration sensor; detecting ambient noise using a microphone; generating a vibrational noise-canceling signal; generating, an ambient noise-canceling signal; and controlling, by the processing circuit, a speaker to provide the vibrational noise-canceling signal, the ambient noise-canceling signal, and a desired sound signal.

Another embodiment relates to a method for canceling vibrational noise sound waves detected in a listener's temporal bones. The method includes receiving a plurality of inputs, including a first input based on a vibration traveling toward a listener's ear, a second input based on a vibration traveling away from the listener's ear, a third input based on a sound traveling toward the listener's ear, and a fourth input based on a sound traveling away from the listener's ear; generating a noise mitigation signal to at least partially cancel the first input and the third input; and controlling, by the processing circuit, operation of a speaker to apply the noise mitigation signal and a desired sound signal to a listener.

Another embodiment relates to a method for canceling vibrational noise sound waves detected in a listener's temporal bones. The method includes controlling, by a processing circuit, a speaker configured to play a desired sound signal and a noise mitigation signal, wherein the noise mitigation signal is generated by a processing circuit coupled to at least one vibration sensor and coupled to at least one microphone. The processing circuit detecting the phase, amplitude, and direction of vibrational noise sound waves near a listener's ear using at least one vibration sensor; detecting the phase, amplitude, and direction of ambient noise using at least one microphone; generating the noise mitigation signal based on the phase, amplitude, and direction of the vibrational noise sound waves and the ambient noise; and controlling the speaker to provide the noise mitigation signal and the desired sound signal.

Another embodiment relates to a tangible, non-transitory computer-readable storage medium having machine instructions stored therein, the instructions being executable by a processor to cause the processor to perform various operations. The operations include receiving a signal regarding undesired vibrational noise sound waves at a processing circuit; receiving a signal regarding undesired ambient sound waves at the processing circuit; and controlling, by the processing circuit, a speaker to provide a desired sound signal and a noise mitigation signal configured to at least partially cancel undesired sound waves.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
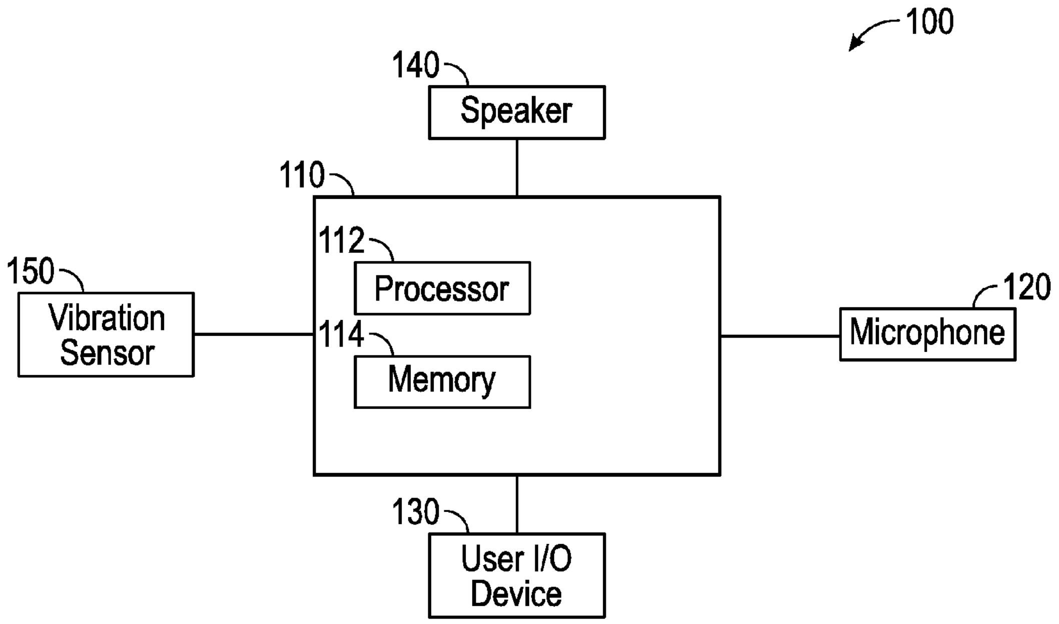
FIG. 1 is an illustration of a noise-canceling earphone according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, systems and methods for delivering desired audible signals to a listener while actively canceling undesired noises are shown according to various embodiments. Some earphones, including in-ear-canal headphones ("canalphones"), canalbuds, and full-size headphones, are designed to block undesired external noises by plugging the listener's ear drum or creating a cushioned seal around the listener's entire ear. Some earphones, known as noise-canceling headphones, attempt to cancel undesired outside noises using active noise cancellation techniques by sampling outside sound and then feeding an inverse audio signal to the listener to cancel out or reduce unwanted background noises. One way that undesired noise bypasses earphones, including noise-canceling earphones, is that it creeps around the earphones by conduction within the temporal bones behind the listener's ear. Although some earphones intend to completely block out outside noises, undesired noise still enters the listener's ear through vibrations in the listener's skull, most notably in the listener's temporal bones surrounding the ear. Listeners may view this sound as annoying, irritating, unpleasant, or aesthetically unpleasing. According to various embodiments disclosed herein, a processing circuit controls operation of at least one vibration sensor, at least one microphone, and at least one speaker in a noise-canceling device to provide a mitigation signal to the listener that cancels or substantially cancels unwanted outside noises, including those that enter the listener's ear through vibrations in the listener's temporal bones. Accordingly, the listener will hear higher-quality audio signals with less or no interference from undesired background noises.

Figure 2:
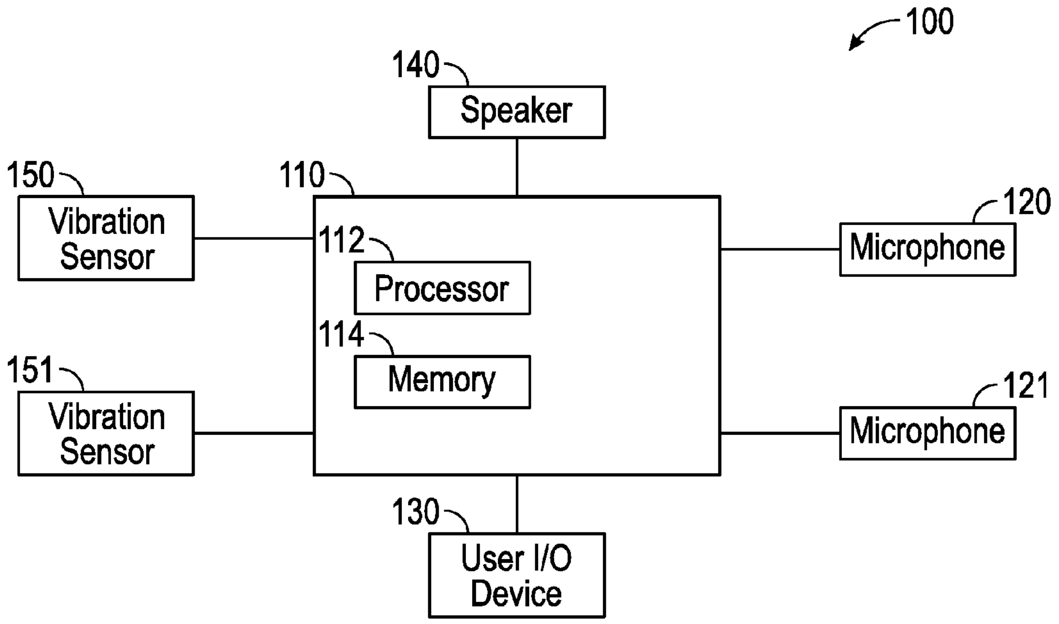
FIG. 2 is an illustration of the noise-canceling earphone according to one embodiment.
Figure 3A:
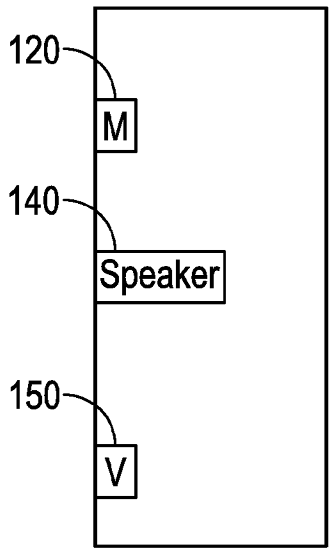
FIGS. 3A-3C are illustrations of noise-canceling earphones according to separate embodiments.
Figure 3B:
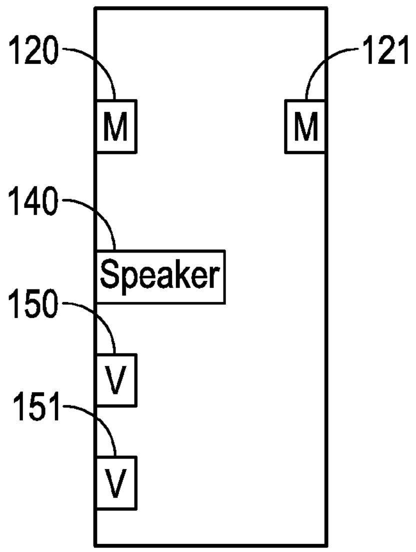
Figure 3C:
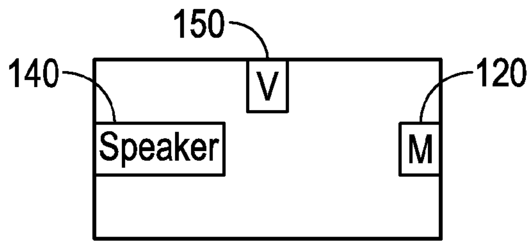
Figure 4:
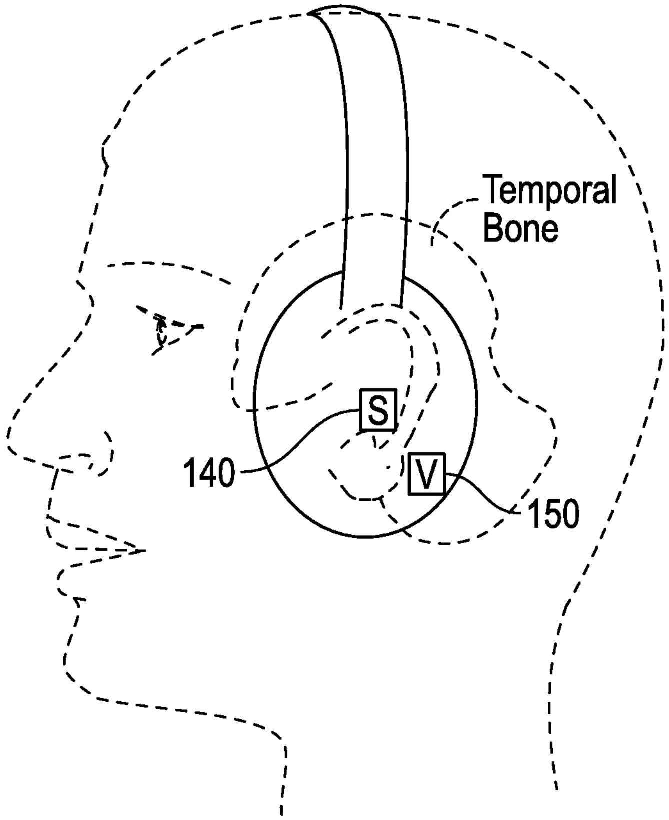
FIG. 4 is an illustration of the noise-canceling earphone according to one embodiment.

Referring now to FIG. 1, noise-canceling device 100 is shown according to one embodiment. Typically, noise-canceling device 100 is utilized with input/output device 130, such as a mobile device, an MP3 player, a CD player, stereo system, television, computer, tablet computer, personal digital assistant ("PDA"), watch, virtual reality system, virtual glasses, etc. When utilized with input/output device 130, noise-canceling device 100 may receive input from input/output device 130 using a headphone cable, USB cable, Bluetooth technology, wireless technology, etc. As shown, noise-canceling device 100 generally includes processing circuit 110, microphone 120, input/output device 130, speaker 140, and vibration sensor 150. As shown in FIG. 2, noise-canceling device 100 may use multiple vibration sensors 150, 151 and multiple microphones 120, 121 to detect undesired noises. In some embodiments, noise-canceling device 100 may not use microphones. Furthermore, as shown in FIGS. 3A-3C, the location of elements of noise-canceling device 100 are not limited. For example, noise-canceling device 100 may take many forms and vibration sensors 150, 151, microphones 120, 121, and speaker 140, may be located in different positions. As shown in FIG. 4, it can be beneficial for vibration sensor 150 to be located directly over a listener's temporal bones. It may be of benefit for vibration sensor 150 to be located as far as possible from speaker 140 in order to provide processing circuit 110 ample time to generate a mitigation signal.

In operation, noise-canceling device 100 receives an input from input/output device 130. Input/output device 130 typically provides a desired audio signal to noise-canceling device 100. In many cases, the desired audio signal will include music, radio, speeches, podcasts, lectures, or other audible signals that the listener desires to hear without disturbance from background noises. The listener is not limited, however, to listening to audible signals without disturbance from background noises. In some embodiments, as discussed further below, the noise-canceling earphone includes a control system that is configured to selectively provide the mitigation signal.

As used herein, the phrase "noise-canceling device" may refer to many types of listening devices, including single-ear earpieces or single-ear earphones or listening devices comprising a plurality of earphones or speakers. In many instances, this disclosure focuses on a single earphone or multiple earphones used or worn by a single individual; however, the noise-canceling device may be employed in a wide range of embodiments, including, for example, surround sound movie experiences, listening devices, gaming systems, therapy booths, tranquility pods, multi-participant listening experiences, etc. The noise-canceling device is not limited to use by a single individual and may employ a plurality of sensors, microphones, speakers, processing circuits, etc. to permit multiple participants to enjoy the same or similar desired audio signals clarified and enhanced through the noise-canceling device. When intended for use by multiple listeners, the device may provide control units for multiple listeners to adjust the level of noise-cancellation to their own preference. The phrase "mitigation signal" may refer to either a vibrational noise-canceling signal, an ambient noise-canceling signal, or both in combination. Further, the mitigation signal, vibrational noise-canceling signal, or ambient noise-canceling signal may be any type of signal that interferes with undesired noise, including a vibrational signal or audible sound signal.

Referring back to FIG. 1, vibration sensor 150 detects vibrational noise sound waves near a listener's ear. In some embodiments, vibration sensor 150 is an accelerometer located either near a listener's temporal bones or in conduction with the listener's temporal bones, in some instances, by resting on the skin overlying the bones. Vibration sensor 150 may also detect vibrations using a piezoelectric sensor, detecting skin or bone motion via reflections of electromagnetic radiation (e.g., using a laser or radar), etc. Vibration sensor 150 may detect the strength of the vibrational noise sound waves (e.g., their amplitude, intensity, etc.). Vibration sensor 150 may detect a frequency dependence of the vibrational noise sound waves (e.g., strength at a specific frequency, strength at a plurality of frequencies, relative strength at a plurality of frequencies, presence of an above threshold strength at one or more frequencies, etc.). Vibration sensor 150 may also detect vibrations by delivering an ultrasonic wave into the temporal bones, and detecting changes to the ultrasonic wave due to nonlinear interactions of the ultrasonic wave and the vibrational sound waves. These changes to the ultrasonic wave can include the generation of scattered ultrasonic waves, the generation of frequency-shifted ultrasonic waves, etc. The nonlinearly induced changes in the ultrasonic wave generally depend on the relative propagation direction of the vibrational noise sound waves and the ultrasound waves, and thus can be used to determine the direction of the vibrational noise sound waves. Vibration sensor 150 may also include various directional properties, such that vibration sensor 150 detects and receives all or most of the vibrational sound waves in the listener's temporal bones. For example, vibration sensor 150 may include omnidirectional, bidirectional, and unidirectional characteristics, where the directionality characteristics indicate the directions that vibration sensor 150 may detect vibrational sounds waves from (e.g., omnidirectional vibration sensor picks up sound evenly or substantially evenly from all directions).

In operation, vibration sensor 150 receives the vibrational sound waves in a pressure wave format (i.e., vibrational sound). Vibration sensor 150 converts the vibrational sound into an electrical energy format, and transmits this electrical energy to processing circuit 110. In turn, processing circuit 110 determines an electrical signal corresponding to a vibrational noise-canceling signal that at least partially cancels the vibrational noise sound waves. Processing circuit 110 provides the determined electrical signal to speaker 140. Speaker 140 converts the electrical signal to an audible mitigation signal and emits the audible mitigation signal to at least partially cancel the vibrational noise sound waves. In other embodiments, processing circuit 110 may provide the determined electrical signal to a vibratable element, in which case the vibratable element converts the electrical signal to a vibrational noise-canceling signal and emits the vibrational noise-canceling signal to at least partially cancel the vibrational noise sound waves. Vibratable element may provide the vibrational noise-canceling signal to various locations, including to air in communication with the listener's cochlea or to the listener's temporal bones. Delivery of the vibrational noise-canceling signal to the listener's temporal bones may be done directly (e.g., via a subdermal or transdermal implant in direct contact with the temporal bones). Alternatively, delivery of the vibrational noise-canceling signal to the listener's temporal bones may be done indirectly (e.g., via vibrating the skin above the temporal bones).

In some embodiments, noise-canceling device 100 may include microphone 120. Microphone 120 may include dynamic, condenser, ribbon, crystal, or other types of microphones. Microphone 120 may include various directional properties, such that microphone 120 detects and receives all or most of the undesired ambient (i.e., atmospheric) sound waves. For example, microphone 120 may include omnidirectional, bidirectional, and unidirectional characteristics, where the directionality characteristics indicate the directions that microphone 120 may detect sound from (e.g., omnidirectional microphone picks up sound evenly or substantially evenly from all directions). In operation, microphone 120 receives ambient sound waves in an acoustical format (i.e., audible noise). Microphone 120 converts the audible noise into an electrical energy format, and transmits this electrical energy to processing circuit 110. In turn, processing circuit 110 determines an electrical signal corresponding to an audible mitigation sound that at least partially cancels the undesired ambient sound waves. Processing circuit 110 provides the determined electrical signal to speaker 140. Speaker 140 converts the electrical signal to an audible mitigation sound and emits the audible mitigation sound to at least partially cancel the ambient sound. Speaker 140 may provide the vibrational noise-canceling signal to various locations, including to air in communication with the listener's cochlea or (directly or indirectly) to the listener's temporal bones.

As shown in FIG. 1, processing circuit 110 includes processor 112 and memory 114. Processor 112 may be implemented as a general-purpose processor, an application specific integrated circuit (ASIC), one or more field programmable gate arrays (FPGAs), a digital-signal-processor (DSP), a group of processing components, or other suitable electronic processing components. Memory 114 is one or more devices (e.g., RAM, ROM, Flash Memory, hard disk storage, etc.) for storing data and/or computer code for facilitating the various processes described herein. Memory 114 may be or include non-transient volatile memory or non-volatile memory. Memory 114 may include database components, object code components, script components, or any other type of information structure for supporting the various activities and information structures described herein. Memory 114 may be communicably connected to processor 112 and provide computer code or instructions to processor 112 for executing the processes described herein.

Processing circuit 110 may receive one or more inputs from vibration sensor 150, microphone 120, and/or input/output device 130. Vibration sensor 150 may detect the vibrational sound waves in the listener's temporal bones caused by undesired ambient noise and transmit an electrical signal based on the vibrational sound waves to processing circuit 110. In addition to this input, microphone 120 may detect undesired ambient noise approaching the listener and transmit an electrical signal based on that noise to processing circuit 110. However, the vibrational sound waves detected in the listener's temporal bones may include both a first component directed toward the listener's ears as well as a second component which is directed away from the listener's ears (or which laterally bypasses the ears). In such situations, generating and applying to the ear a vibrational noise-cancelling signal based on the second component would actually degrade listening performance (since the noise-cancelling signal arrives but the purported noise does not). Similarly, the ambient noise may include both a third component directed toward the listener's ears as well as a fourth component which is directed away from the listener's ears (or which laterally bypasses the ears). In such situations, generating and applying to the ear an ambient noise-cancelling signal based on the fourth component would actually degrade listening performance (since the noise-cancelling signal arrives but the purported noise does not). For example, in one embodiment, processing circuit 110 is configured to receive a first input based on a vibration traveling toward a listener's ear, a second input based on a vibration traveling away from the listener's ear, a third input based on an atmospheric sound traveling toward the listener's ear, and a fourth input based on an atmospheric sound traveling away from the listener's ear. Processing circuit 110, based on the inputs, can then determine which vibration signals are desired and which vibration signals are not desired, as well as which atmospheric sounds are desired and which atmospheric sounds are not desired. Typically, processing circuit 110 is configured to cancel vibrations and ambient sound traveling toward the listener's ear, but not to cancel vibrations or ambient sound which are directed away from the listener's ear. Therefore, in this example, processing circuit 110 would determine a noise mitigation signal to at least partially cancel the first input and the third input. Finally, processing circuit 110 controls operation of a speaker to provide the noise mitigation signal and a desired sound signal. In another embodiment, microphone 120 is either not present or is unused, so that processing circuit 110 addresses only the vibrational noise (i.e., the first and second inputs) but not ambient noise (i.e., the third and fourth inputs).

In addition to the inputs described above, processing circuit 110 may receive inputs via input/output device 130. For example, as discussed above, processing circuit 110 may receive an input from input/output device 130 to selectively provide noise mitigation signals. According to one embodiment, the input includes an activation or deactivation of processing circuit 110. Processing circuit 110 may also receive a mitigation signal setting input. The mitigation signal setting input may include a frequency, a phase, and/or an amplitude input, among others, that affects the characteristics of the mitigation signal emitted by speaker 140. For instance, a frequency input may indicate that the mitigation signal should preferentially cancel low frequency components of the undesired vibrational sound waves, or alternatively, that it should preferentially cancel high frequency components. A phase input may indicate a phase shift which the mitigation signal sound should apply to the undesired vibrational sound. In one embodiment a 180 degrees phase shift is used to maximize cancellation (i.e., a phase inverted mitigation signal relative to the undesired vibrational sound waves). An amplitude input may indicate an absolute amplitude level for the mitigation signal, or may indicate a mitigation amplitude relative to that of undesired vibrational noise waves. Accordingly, the modified audible mitigation signal may completely cancel or only partially cancel the undesired vibrational noise waves (see FIGS. 5A-5E).

For example, using input/output device 130, the listener may adjust the level of noise-cancellation to a desired level in order to completely cancel undesired noises or to allow some background noises to be heard. Processing circuit 110 can be configured to receive an input to control operation of the speaker to provide the mitigation signal at a predetermined amplitude and duration. In some embodiments, the processing circuit is configured to selectively provide an ambient noise-canceling signal, a vibrational noise-canceling signal, or both, depending on the listener's preference. Such control may be desired if the listener wishes to not completely cancel or block background noises and be more aware of surroundings. For example, a listener may not wish to completely block or cancel background noises while riding a bicycle, crossing a street, listening to announcements, etc. In some instances, the listener may configure the noise-canceling device to completely block out all ambient noise with the exception of certain frequencies. In some instances, the listener may configure the noise-canceling device to adjust a time delay used by the device between its detection of an undesired sound (bone vibrations or atmospheric) and its delivery of a mitigation sound. Processing circuit 110 may also operate in multiple distinct modes, where the mode selection is received via input/output device 130.

Referring now to FIGS. 5A-5E, the canceling and partial canceling effects of the mitigation signal are shown according to various embodiments. In regard to FIGS. 5A-5E, the sound waves depicted refer to the undesired sound, for example, the detected vibrational noise sound waves or detected ambient noise, or both. Accordingly, as seen in FIGS. 5A-5E, the mitigation signal interacts with the undesired sound to create a resultant sound wave. Sound propagates through a medium (e.g., air, skin, bone) as a waveform, which enables other waveforms to either constructively or destructively interfere. Destructive interference refers to reduction of the propagating sound wave (e.g., the audible noise may be reduced). In comparison, constructive interference refers to an increase of the propagating sound wave (e.g., the propagating wave and other wave are added together upon their interaction). According to various embodiments disclosed herein, the mitigation signal destructively interferes with the undesired sound detected by vibration sensor 150 or microphone 120, or both, to cancel or partially cancel the undesired sound's audible level.

Figure 5A:
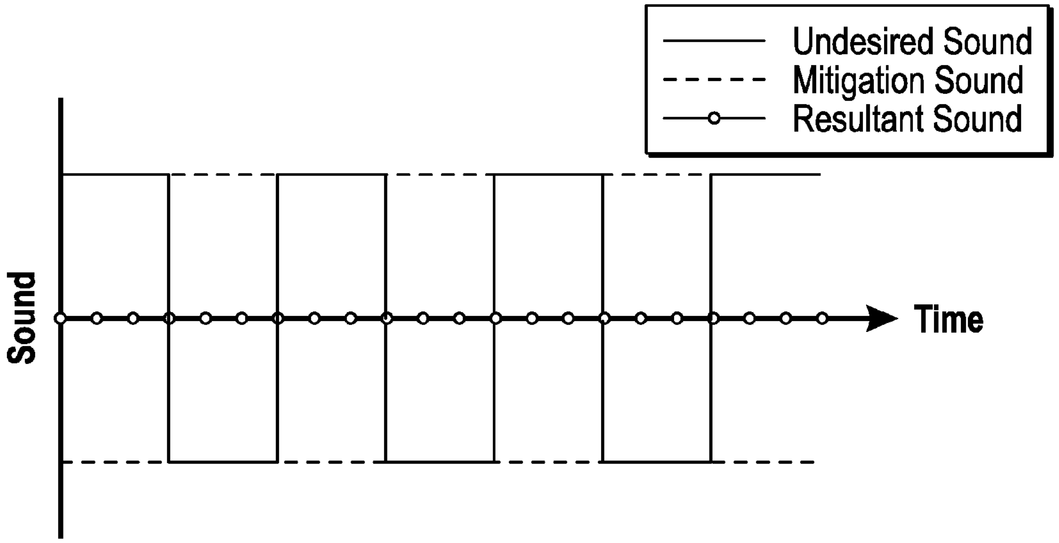
FIGS. 5A-5D are diagrams of mitigation sound waves interfering with sound waves generated by vibrations in a listener's temporal bones according to one embodiment.
Figure 5B:
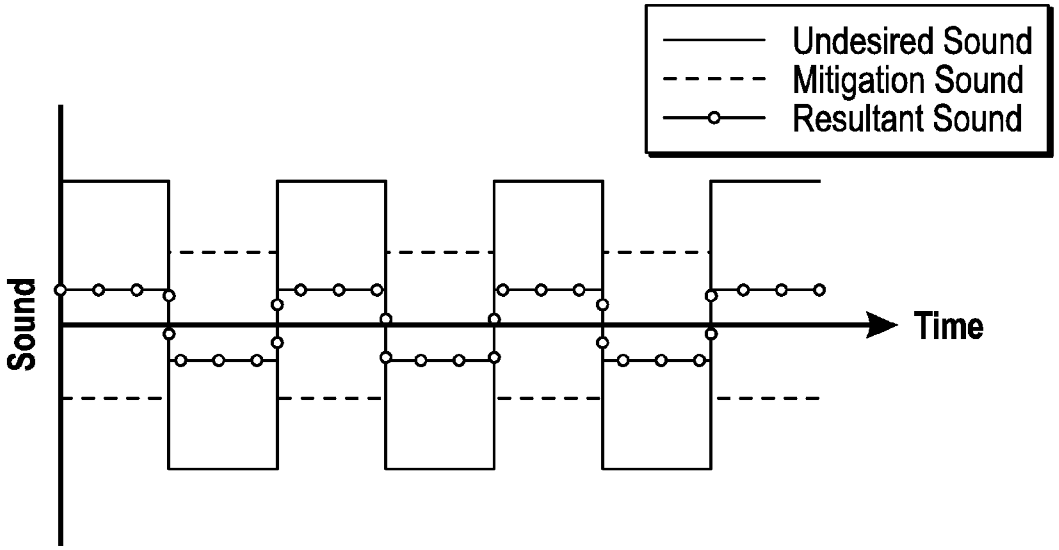
Figure 5C:
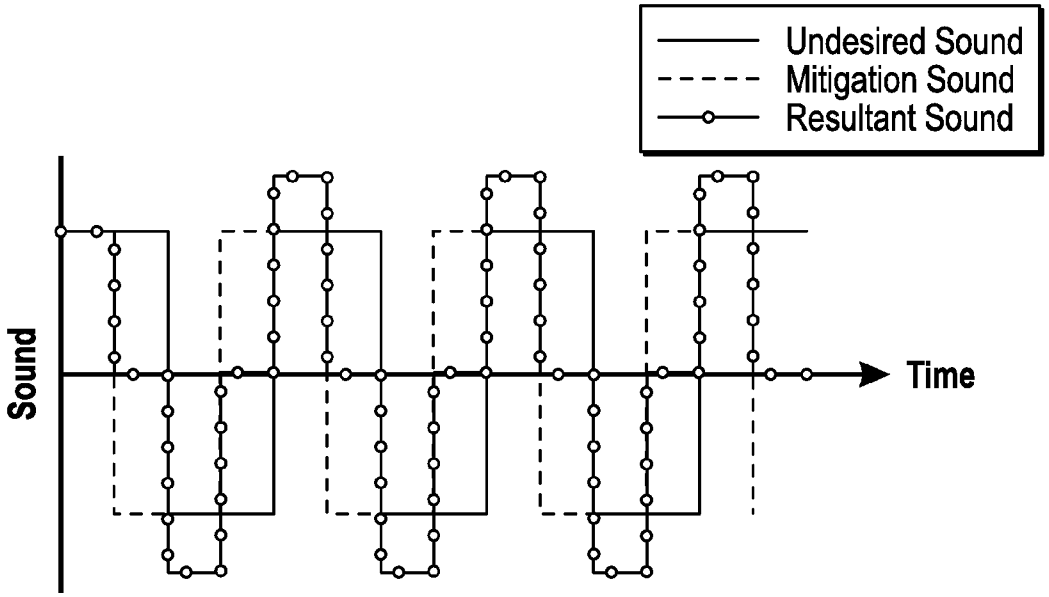
Figure 5D:
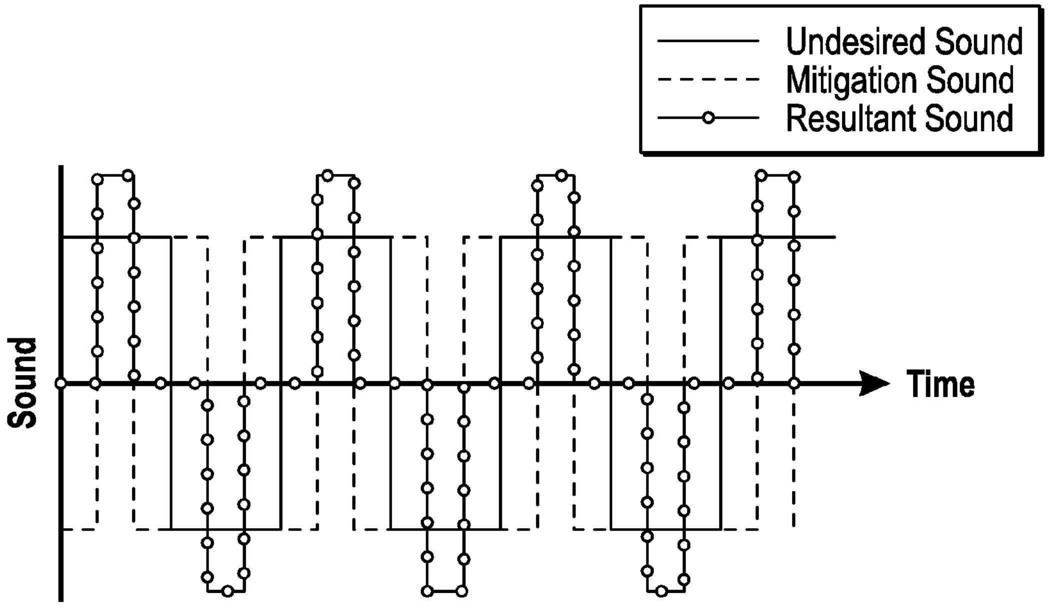
Figure 5E:
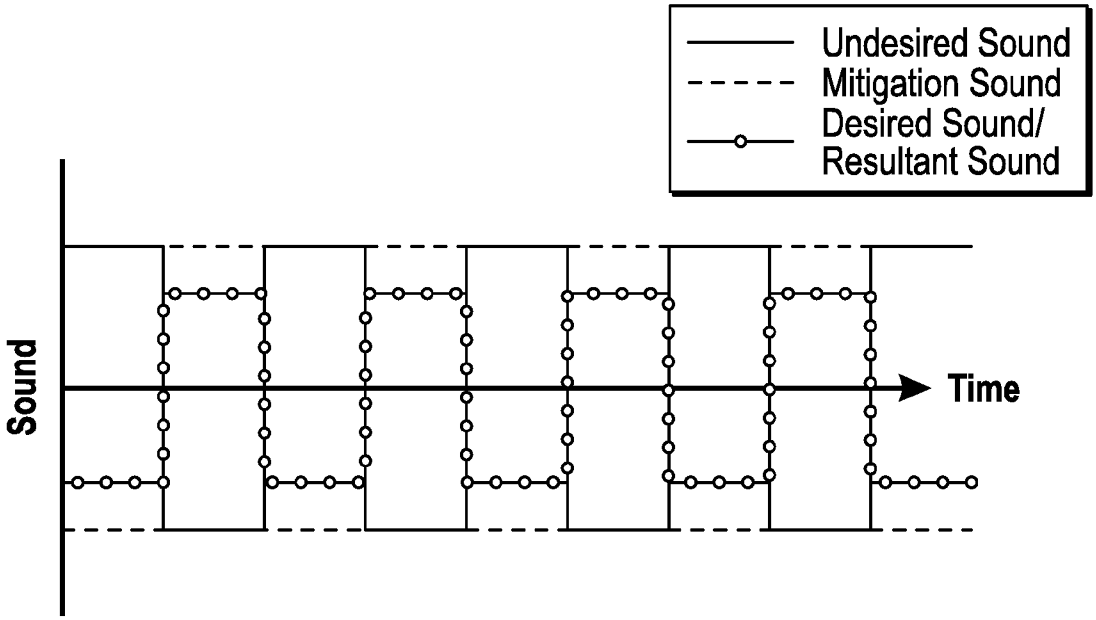
FIG. 5E is a diagram of mitigation sound waves interfering with sound waves generated by undesired vibrations in a listener's temporal bones and the resulting desired sound waves provided to a the listener.

Referring more particularly to FIG. 5A, processing circuit 110, via speaker 140, provides a mitigation signal of the same frequency and amplitude as that of the shown undesired sound. The two waveforms are of the same amplitude and completely out-of-phase, such that they interact to produce zero audible sound (see resultant sound wave). In this embodiment, the listener using noise-canceling device 100 does not hear the undesired noise, whether from vibrational noise sound waves in the listener's temporal bones or from ambient noise. In this example, if a desired sound signal were also provided by speaker 140, the listener would not hear any of the undesired noise and would only hear the desired sound signal, as shown in FIG. 5E. According to various alternate embodiments, the mitigation signal may have an amplitude less than that of the undesired sound, such that the level of the undesired sound is reduced so that the listener may hear some sound from their surroundings.

In some embodiments, processing circuit 110 receives inputs, such as frequency, phase, and/or amplitude inputs, that adjust the mitigation signal characteristics via input/output device 130. Accordingly, the resultant sound (represented in FIGS. 5A-5E as the dash-dot-dash line) produced by the interaction of the mitigation signal and the desired sound signal may be adjusted. For example, in FIG. 5B, the mitigation signal is at a relatively lesser amplitude but the same frequency as the undesired sound. Accordingly, the resultant sound does not completely cancel the undesired sound wave. As such, the undesired sound may be heard by a user of the device (dependent on the location of the user in relation to the device). In comparison, FIG. 5C depicts a mitigation signal of the same amplitude but of a different phase as the undesired sound wave. As such, the undesired sound may be either canceled to a shorter duration, or increased in audible level due to constructive interference. Similarly, in FIG. 5D, the frequency of the mitigation signal has been increased relative to the frequency of the undesired sound wave. As such, the undesired sound may be either canceled to a shorter duration, or increased in audible level due to constructive interference. Thus, according to various embodiments, processing circuit 110 may enable adjustment of the duration and volume of the undesired sound from its interaction with the mitigation signal via inputs, such as frequency, phase, and amplitude inputs, from input/output device 130.

In some embodiments, the mitigation signal is provided to different locations in relation to a listener's ear to at least partially cancel undesired sounds. In many cases, the mitigation signal is applied near or in a listener's ear using a speaker. In this case, the mitigation signal is applied to air in communication with the listener's cochlea. In some embodiments, the vibrational noise-canceling signal is applied (directly or indirectly) to the listener's temporal bones through a vibratable element, speaker, etc. In some cases, it may be beneficial to provide the mitigation signal separately to the air in communication with the listener's cochlea and to the listener's temporal bones. The same mitigation signal may be applied to both locations or separate mitigation signals may be applied to separate locations (e.g., the vibrational noise-canceling signal is applied to the listener's temporal bones and the ambient noise-canceling signal is applied to the air in communication with the listener's cochlea) in order to target different types of undesired noise sound waves (e.g., undesired noise caused by vibrations in the temporal bones and undesired noise traveling through air in the ear canal of a listener). In any of the examples above, in combination with a mitigation signal, the desired sound signal may be applied to air in communication with the listener's cochlea through speaker 140 and/or to the listener's temporal bones through a vibratable element. In this example, the desired sound signal is applied to the listener's temporal bones and travels through the temporal bones to the cochlea.

In some embodiments, noise-canceling device 100 detects undesired noise at a distance further away from the listener's cochlea in comparison with the location of speaker 140. In these embodiments, the undesired noise is detected further away from the application point of the mitigation signal (e.g., provided by speaker 140 or vibratable element, etc.) to enable processing circuit 110 to have enough time to generate the mitigation signal, combine the mitigation signal with the desired sound signal, and to provide the combined signal to speaker 140 so that all sound waves (desired and undesired) reach the listener's cochlea at the same time. For example, in one embodiment, speaker 140 is located one centimeter away from the listener's cochlea and vibration sensor 150 is located three centimeters away from the listener's cochlea, which provides processing circuit 110 with two centimeters worth of undesired sound wave travel time to generate the mitigation signal and provide it to speaker 140. In some embodiments, for example on a traditional headphone, vibration sensor 150 is located on the rim of the headphone, which when worn by a listener would be pressed against the listener's temporal bones behind the earlobe. Microphone 120 may be located opposite speaker 140 on the outside of the earphone directed away from the listener. In another embodiment, for example on a canalphone, vibration sensor 150 is located on the portion of the rim of the canalphone that is inserted into the listener's ear canal. Microphone 120 may be located opposite speaker 140 on the outside of the canalphone directed away from the listener.

In some embodiments, noise-canceling device 100, through processing circuit 110, delays providing the mitigation signal so that the mitigation signal and the undesired sound arrives at the listener's cochlea at the same time. As discussed above, to at least partially cancel an undesired sound wave, a mitigation signal that is out-of-phase with the undesired sound wave is delivered to a listener's ear simultaneously. Therefore, to ensure the mitigation signal and the undesired sound wave reach the listener's ear at the same time, processing circuit 110 may be configured to delay providing the mitigation signal. For example, in one embodiment, processing circuit 110 detects undesired noise, generates a mitigation signal, delays providing the mitigation signal to speaker 140 for an appropriate time (e.g., 10 microseconds), and provides the mitigation signal to speaker 140, which arrives at the cochlea at the same or at a substantially similar time as the undesired sound signal, thereby at least partially canceling the undesired sound. Processing circuit 110 may determine how long of a delay is necessary, if any, by using multiple microphones or multiple vibration sensors to determine the speed at which the undesired sound waves are traveling, or may determine the speed using predetermined values for sound speed in the temporal bones, in the atmosphere, etc. Furthermore, processing circuit 110 may separately delay provision of the vibrational noise-canceling signal and the ambient noise-canceling signal based on determining that one undesired sound is traveling faster than the other. In one embodiment, processing circuit 110 may be configured to detect and cancel ambient sound waves in the ear canal of a listener using a microphone or vibration sensor located in the ear canal. For example, processing circuit 110 may be configured to detect ambient sound waves in the listener's ear canal using a microphone, generate an ambient noise-canceling signal, and control operation of the speaker to provide the ambient noise-canceling signal. In this example, processing circuit 110 may also control the speaker to delay providing the ambient noise-canceling signal so that the ambient noise-canceling signal and the ambient sound waves arrive at the listener's cochlea at the same time.

In some embodiments, noise-canceling device 100 includes a plurality of sensors, including multiple microphones and/or multiple vibration sensors, to measure sound waves at a plurality of points. It may be beneficial to measure sound waves at multiple locations to determine which sounds waves are traveling toward the listener's ear and which sound waves are traveling away from the listener's ear. Such a measurement enables processing circuit 110 to determine which sound should be provided to the listener and which sound is undesired and should be canceled out. For example, in many cases, speaker 140 causes sound waves to be generated in all directions, thus causing desired sound signals to travel toward the listener's ear and causing desired sound signals to travel away from the listener's ear. Undesired noises are commonly generated by the environment that surround the listener; therefore, locally detected undesired noises are generally traveling toward the listener. By detecting which sound waves are traveling toward (e.g., undesired, and desired) the listener and which sound waves are traveling away from (e.g., desired) the listener, processing circuit 110 may differentiate between the undesired and desired sound and generate a mitigation signal to at least partially cancel the undesired sound waves. In generating a mitigation signal, processing circuit 110 may be configured to predict the strength of the undesired sound once it reaches the listener and to predict the time that the undesired sound will reach the listener.

Figure 6:
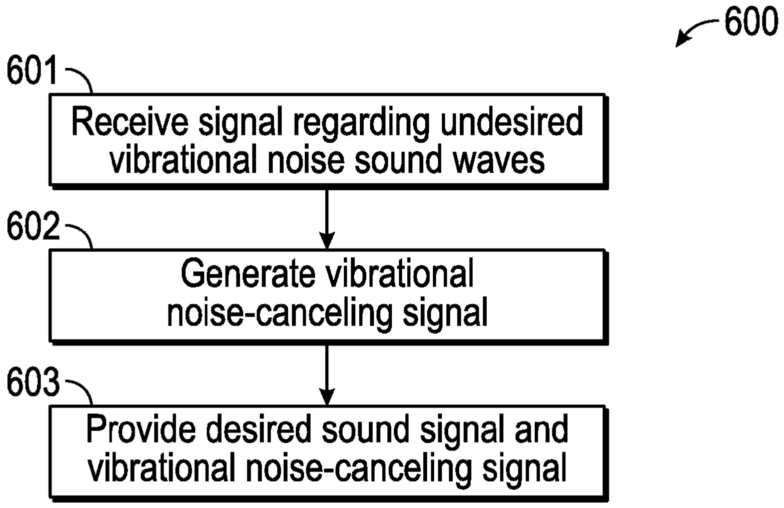
FIG. 6 is a diagram of a method for canceling vibrational noise sound waves according to one embodiment.

Referring next to FIG. 6, method 600 for cancelling vibrational noise sound waves detected in a listener's temporal bone is shown according to one embodiment. According to one embodiment, method 600 may be a computer-implemented method utilizing device 100. Method 600 may be implemented using any combination of computer hardware and software. According to one embodiment, method 600 is implemented when the noise-canceling device is turned on by a listener, commonly through an input delivered through input/output device 130. A signal regarding undesired vibrational noise sound waves is received (601). A vibrational noise-canceling signal is generated (602), for example, by processing circuit 110. Speaker 140 is controlled (e.g., by processing circuit 110) to provide a desired sound signal and the vibrational noise-canceling signal (603). As discussed above, the provided mitigation sound may partially or completely cancel the undesired vibrational noise sound waves and/or provide a desired sound signal (see FIGS. 5C-5E).

Figure 7:
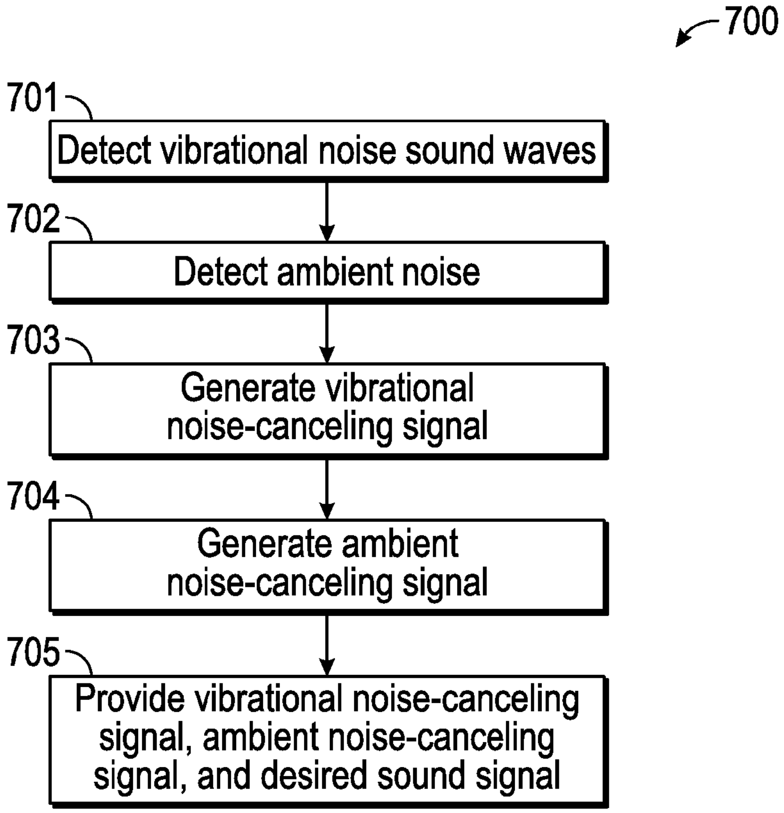
FIG. 7 is a diagram of a method for canceling vibrational noise sound waves and ambient sound waves according to one embodiment.

Referring next to FIG. 7, method 700 for cancelling vibrational noise sound waves detected in a listener's temporal bone is shown according to one embodiment. According to one embodiment, method 700 may be a computer-implemented method utilizing device 100. Method 700 may be implemented using any combination of computer hardware and software. According to one embodiment, method 700 is implemented when the noise-canceling device is turned on by a listener, commonly through an input delivered through user input/output device 130. Vibrational noise sound waves near a listener's ear are detected, for example, using vibration sensor 150 (701). Ambient noise is detected, for example, using microphone 120 (702). A vibrational noise-canceling signal (703) and an ambient noise-canceling signal (704) is generated. Speaker 140 is controlled (e.g., by processing circuit 110) to provide the vibrational noise-canceling signal, the ambient noise-canceling signal, and a desired sound signal (705).

Figure 8:
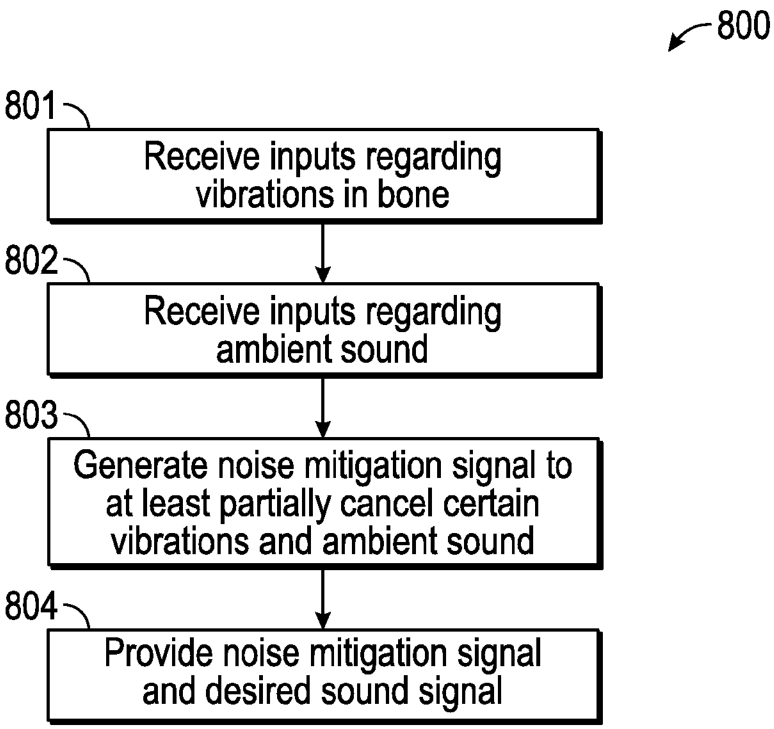
FIG. 8 is a diagram of a method for canceling vibrational noise sound waves and ambient sound waves based on reception of various inputs.

Referring next to FIG. 8, method 800 for cancelling vibrational noise sound waves detected in a listener's temporal bone is shown according to one embodiment. According to one embodiment, method 800 may be a computer-implemented method utilizing device 100. Method 800 may be implemented using any combination of computer hardware and software. According to one embodiment, method 800 includes receiving a plurality of inputs regarding vibrations in bone (801). A first input based on a vibration traveling toward a listener's ear and a second input based on a vibration traveling away from the listener's ear is received, for example, by processing circuit 110. A plurality of inputs regarding ambient sound (802) are also received. A third input based on a sound traveling toward the listener's ear and a fourth input based on a sound traveling away from the listener's ear is received, for example, by processing circuit 110. A noise mitigation signal is generated (e.g., by processing circuit 110) to at least partially cancel the first input and the third input (i.e., vibrations and/or sound traveling toward the listener's ear) (803). The noise mitigation signal and a desired sound signal is provided to speaker 140 (804) (e.g., by processing circuit 110).

Figure 9:
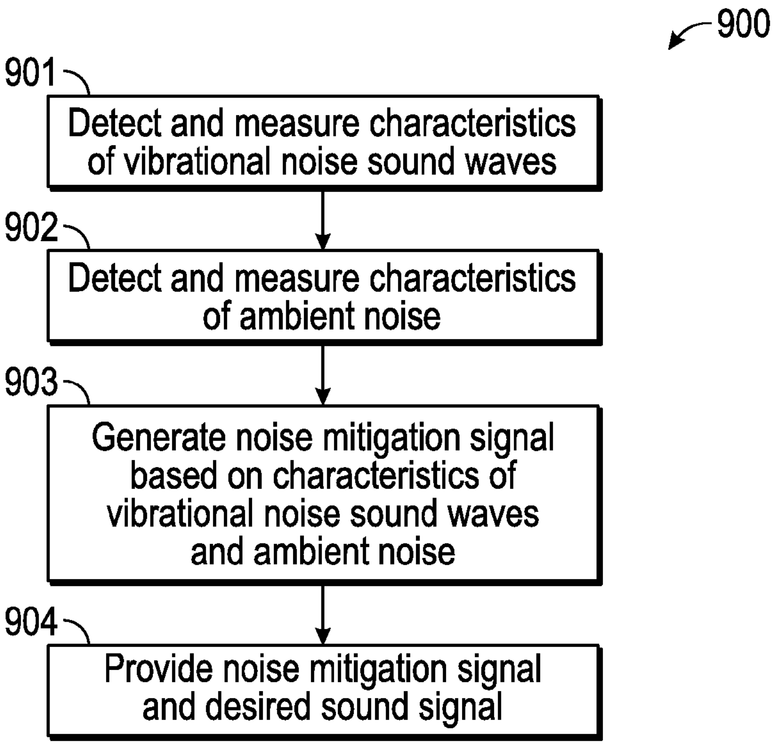
FIG. 9 is a diagram of a method for canceling vibrational noise sound waves and ambient sound waves based on characteristics of the undesired sound.

Referring next to FIG. 9, method 900 for cancelling vibrational noise sound waves detected in a listener's temporal bone is shown according to one embodiment. According to one embodiment, method 900 may be a computer-implemented method utilizing device 100. Method 900 may be implemented using any combination of computer hardware and software. The phase, amplitude, and direction of vibrational noise sound waves near a listener's ear are detected, for example, using vibration sensor 150 (901). The phase, amplitude, and direction of ambient noise is detected, for example, using microphone 120 (902). The noise mitigation signal is generated (e.g., by processing circuit 110) based on the phase, amplitude, and direction of the vibrational noise sound waves and the ambient noise (903). The noise mitigation signal and the desired sound signal is provided to speaker 140 (904) (e.g., by processing circuit 110).

Methods 600, 700, 800, and 900, as shown in FIGS. 6-9, may incorporate any feature described above, including features analogous to those described in relation to device 100.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A noise-canceling earphone, comprising:

a vibration sensor configured to detect vibrational noise sound waves in a listener's skin proximate the listener's temporal bones, the vibrational noise sound waves having a first component traveling toward the listener's ear and a second component traveling away from the listener's ear;

a speaker; and a processing circuit configured to:

receive an input signal regarding the vibrational noise sound waves from the vibration sensor;

generate a vibrational noise-canceling signal based on a comparison of the first component with the second component, the vibrational noise-canceling signal configured to at least partially cancel the first component of the vibrational noise sound waves; and control operation of the speaker to provide a desired sound signal and the vibrational noise-canceling signal to at least partially cancel the first component of the vibrational noise sound waves.

2. The noise-canceling earphone of claim 1, wherein the vibration sensor detects vibrations using at least one of a laser, a radar, and a piezoelectric sensor.

3. The noise-canceling earphone of claim 1, wherein the vibration sensor detects the strength of the vibrations at a plurality of different frequencies.

4. The noise-canceling earphone of claim 1, wherein the vibrational noise sound waves are detected in the listener's skin proximate the temporal bones and in the listener's temporal bones.

5. The noise-canceling earphone of claim 1, wherein the vibrational noise-canceling signal is applied directly to at least one of the listener's temporal bones and the listener's skin proximate the temporal bones.

6. The noise-canceling earphone of claim 5, wherein the desired sound signal is applied directly to at least one of the listener's temporal bones and the listener's skin proximate the temporal bones.

7. The noise-canceling earphone of claim 1, wherein the speaker is located closer to the listener's ear than the vibration sensor.

8. The noise-canceling earphone of claim 1, wherein the processing circuit is further configured to predict a time at which the vibrational noise sound waves will reach the listener's cochlea.

9. The noise-canceling earphone of claim 1, wherein the processing circuit is further configured to predict a strength at which the vibrational noise sound waves will reach the listener's cochlea.

10. The noise-canceling earphone of claim 1, wherein the processing circuit controls the speaker to delay providing the vibrational noise-canceling signal such that the vibrational noise-canceling signal and the vibrational noise sound waves arrive at the listener's cochlea at the same time.

11. The noise-canceling earphone of claim 1, wherein the processing circuit is further configured to detect ambient sound waves in the listener's ear canal using a microphone, generate an ambient noise-canceling signal, and control operation of the speaker to provide the ambient noise-canceling signal.

12. The noise-canceling earphone of claim 1, further comprising one or more microphones configured to detect ambient sound waves, wherein the processing circuit generates an ambient noise-canceling signal based on the detected ambient sound waves, and wherein the processing circuit controls operation of the speaker to provide the ambient noise-canceling signal.

13. A noise-canceling earphone, comprising:

a processing circuit configured to:

receive a plurality of inputs, including a first input based on a vibrational noise sound wave traveling toward a listener's ear, and a second input based on a vibrational noise sound wave traveling away from the listener's ear;

distinguish between the first input and the second input by comparing the direction of the vibrational noise sounds waves of the first input and the direction of the vibrational noise sound waves of the second input, the direction of at least one of the vibrational noise sound waves based on vibrational noise sound waves detected in a listener's skin proximate the listener's temporal bones;

determine a noise mitigation signal to at least partially cancel the first input; and control operation of a speaker to provide the noise mitigation signal.

14. The noise-canceling earphone of claim 13, wherein the plurality of inputs further includes a third input based on a sound traveling toward the listener's ear, and a fourth input based on a sound traveling away from the listener's ear, wherein the listener's ear is only one ear of the listener.

15. The noise-canceling earphone of claim 13, wherein the processing circuit is further configured to control operation of the speaker to provide a desired sound signal.

16. The noise-canceling earphone of claim 13, wherein the vibrational noise sound waves are detected in the listener's temporal bones.

17. The noise-canceling earphone of claim 13, wherein the vibration sensor detects vibrations using a nonlinear interaction with an ultrasonic wave.

18. The noise-canceling earphone of claim 13, wherein the vibration sensor detects a frequency dependence of the vibrations.

19. The noise-canceling earphone of claim 13, wherein the earphone is configured to be wearable by the listener.

20. The noise-canceling earphone of claim 19, wherein at least a portion of the earphone is configured to be inserted into the ear canal of the listener.

21. The noise-canceling earphone of claim 13, wherein the processing circuit is further configured to predict a frequency dependence at which the vibrational noise sound waves will reach the listener's cochlea.

22. The noise-canceling earphone of claim 13, wherein the generation of the vibrational noise-canceling signal is based on a prediction of at least one of a time at which the vibrational noise sound waves will reach the listener's cochlea, a strength at which the vibrational noise sound waves will reach the listener's cochlea, and a frequency dependence at which the vibrational noise sound waves will reach the listener's cochlea.

23. The noise-canceling earphone of claim 13, wherein the processing circuit is configured to selectively provide the ambient noise-canceling signal.

24. The noise-canceling earphone of claim 23, wherein the processing circuit is configured to receive an input to control operation of the speaker to provide the ambient noise-canceling signal at a predetermined amplitude and duration.

25. A tangible, non-transitory computer-readable storage medium having machine instructions stored therein, the instructions being executable by a processor to cause the processor to perform operations comprising:

receiving, by a processing circuit, a first signal regarding undesired vibrational noise sound waves having a first component traveling toward a listener's ear and a second component traveling away from the listener's ear, the undesired vibrational noise sound waves detected in a listener's skin proximate the listener's temporal bones;

receiving, by a processing circuit, a second signal regarding undesired ambient sound waves;

distinguishing between the first component and the second component of the undesired vibrational noise sound waves by comparing the first component with the second component; and controlling, by the processing circuit, a speaker to provide a desired sound signal and a noise mitigation signal, the noise mitigation signal configured to at least partially cancel the first component of the undesired vibrational noise sound waves and the undesired ambient sound waves.

26. The tangible, non-transitory computer-readable storage medium of claim 25, wherein the processing circuit is further configured to detect ambient sound waves in a listener's ear canal using a microphone, generate an ambient noise-canceling signal, and control operation of the speaker to provide the ambient noise-canceling signal.

27. The tangible, non-transitory computer-readable storage medium of claim 26, wherein the processing circuit is configured to selectively provide the ambient noise-canceling signal.

28. The tangible, non-transitory computer-readable storage medium of claim 27, wherein the processing circuit is configured to receive an input to control operation of the speaker to provide the ambient noise-canceling signal at a predetermined amplitude and duration.

29. The tangible, non-transitory computer-readable storage medium of claim 25, further comprising one or more microphones configured to detect ambient sound waves, wherein the processing circuit generates an ambient noise-canceling signal based on the detected ambient sound waves, and wherein the processing circuit controls operation of the speaker to provide the ambient noise-canceling signal.

30. The tangible, non-transitory computer-readable storage medium of claim 29, wherein the one or more microphones includes a first microphone and a second microphone, wherein the first microphone and second microphone measure ambient noise at different locations.

31. The tangible, non-transitory computer-readable storage medium of claim 30, wherein the processing circuit is further configured to predict the strength of the measured ambient noise and to predict the time the ambient noise will reach a listener's cochlea.

32. The tangible, non-transitory computer-readable storage medium of claim 29, wherein the processing circuit controls the speaker to delay providing the ambient noise-canceling signal such that the ambient noise-canceling signal and the ambient sound waves arrive at the listener's cochlea at the same time.

33. The tangible, non-transitory computer-readable storage medium of claim 25, further comprising a plurality of vibration sensors, including a first vibration sensor and a second vibration sensor, wherein the first vibration sensor and second vibration sensor measure vibrational noise sound waves at different locations on a listener's temporal bone.

34. The tangible, non-transitory computer-readable storage medium of claim 33, wherein the processing circuit is further configured to predict the strength of the measured vibrational noise sound waves and to predict the time the vibrational noise sound waves will reach a listener's cochlea.

35. The tangible, non-transitory computer-readable storage medium of claim 25, wherein the processing circuit is configured to receive an input to control operation of the speaker to provide the noise mitigation signal at a predetermined amplitude and duration.

36. The noise-canceling earphone of claim 1, wherein the comparison of the first component with the second component is based on an amplitude of the first component and an amplitude of the second component.

37. The noise-canceling earphone of claim 1, wherein the comparison of the first component with the second component is based on a frequency spectrum of the first component and a frequency spectrum of the second component.

38. The noise-canceling earphone of claim 1, wherein the comparison of the first component with the second component is based on the direction of the first component and the direction of the second component.

* * * * *